(12) United States Patent
Tang et al.

(10) Patent No.: US 11,922,017 B2
(45) Date of Patent: Mar. 5, 2024

(54) COMPACT GENOME DATA STORAGE WITH RANDOM ACCESS

(71) Applicant: Apple Inc., Cupertino, CA (US)

(72) Inventors: Haibao Tang, Mountain View, CA (US); Richard A. Bloomfield, Jr., Cary, NC (US)

(73) Assignee: Apple Inc., Cupertino, CA (US)

( * ) Notice: Subject to any disclaimer, the term of this patent is extended or adjusted under 35 U.S.C. 154(b) by 174 days.

(21) Appl. No.: 17/721,262

(22) Filed: Apr. 14, 2022

(65) Prior Publication Data
US 2022/0342555 A1 Oct. 27, 2022

Related U.S. Application Data

(60) Provisional application No. 63/180,621, filed on Apr. 27, 2021.

(51) Int. Cl.
*G06F 3/06* (2006.01)

(52) U.S. Cl.
CPC .......... *G06F 3/0608* (2013.01); *G06F 3/0655* (2013.01); *G06F 3/0673* (2013.01)

(58) Field of Classification Search
CPC .... G06F 3/0655; G06F 3/0673; G06F 3/0608; G16B 50/50
USPC .......................................................... 711/154
See application file for complete search history.

(56) References Cited

U.S. PATENT DOCUMENTS

| | | | |
|---|---|---|---|
| 10,679,727 B2 | 6/2020 | Ding et al. | |
| 2016/0034638 A1* | 2/2016 | Spence | C12Q 1/6869 702/19 |
| 2017/0286594 A1 | 10/2017 | Reid et al. | |
| 2020/0013483 A1* | 1/2020 | Chang | G16B 50/50 |
| 2021/0150005 A1* | 5/2021 | Pan | G16B 50/40 |

* cited by examiner

*Primary Examiner* — Hashem Farrokh
(74) *Attorney, Agent, or Firm* — BAKERHOSTETLER

(57) ABSTRACT

The subject technology provides compact, searchable, random-access storage of genome data, particularly for large datasets, such as an entire human genome. The genome data may be stored in binary format, and compressed, in part, by leveraging characteristics of genome data itself, and in a way that maintains searchability of the stored compressed data.

20 Claims, 5 Drawing Sheets

COMPACT GENOME DATA STORAGE WITH RANDOM ACCESS

CROSS REFERENCE TO RELATED APPLICATIONS

This application claims the benefit of priority to U.S. Provisional Patent Application No. 63/180,621, entitled, "Compact Genome Data Storage with Random Access", filed on Apr. 27, 2021, the disclosure of which is hereby incorporated herein in its entirety.

TECHNICAL FIELD

The present description generally relates to data compression, including, for example, compact genome storage with random access.

BACKGROUND

With the genome of each individual person including approximately three billion nucleotide pairs, advances in DNA sequencing have created a need for storage of large amounts of genome data.

BRIEF DESCRIPTION OF THE DRAWINGS

Certain features of the subject technology are set forth in the appended claims. However, for purpose of explanation, several embodiments of the subject technology are set forth in the following figures.

DETAILED DESCRIPTION

The detailed description set forth below is intended as a description of various configurations of the subject technology and is not intended to represent the only configurations in which the subject technology can be practiced. The appended drawings are incorporated herein and constitute a part of the detailed description. The detailed description includes specific details for the purpose of providing a thorough understanding of the subject technology. However, the subject technology is not limited to the specific details set forth herein and can be practiced using one or more other implementations. In one or more implementations, structures and components are shown in block diagram form in order to avoid obscuring the concepts of the subject technology.

The subject technology provides for compact, searchable, random-access storage of data such as genome data, including large datasets such as an entire human genome. In various implementations, genome data can be stored compactly, while maintaining random access query capability, by, for example, (i) encoding nucleotide symbols in binary format, (ii) leveraging characteristics of genomic data itself (e.g., including prefix similarities between alleles, homozygous alleles, etc.) for storing the binary encoded nucleotides, (iii) leveraging aspects of Variant Call Format (VCF) data, and/or (iv) bundling records of encoded data.

For example, in one or more implementations, the disclosed operations for encoding the genome data can be applied to VCF data. As discussed in further detail herein, in the example of encoding VCF data, additional encoding and compression efficiencies can be realized, including, for example, by storing the encoded data in records having a record length that is suitable for typical variant records of VCF data, and/or splitting and/or merging intervals in which the genome data being encoded matches the reference genome.

Figure 1:
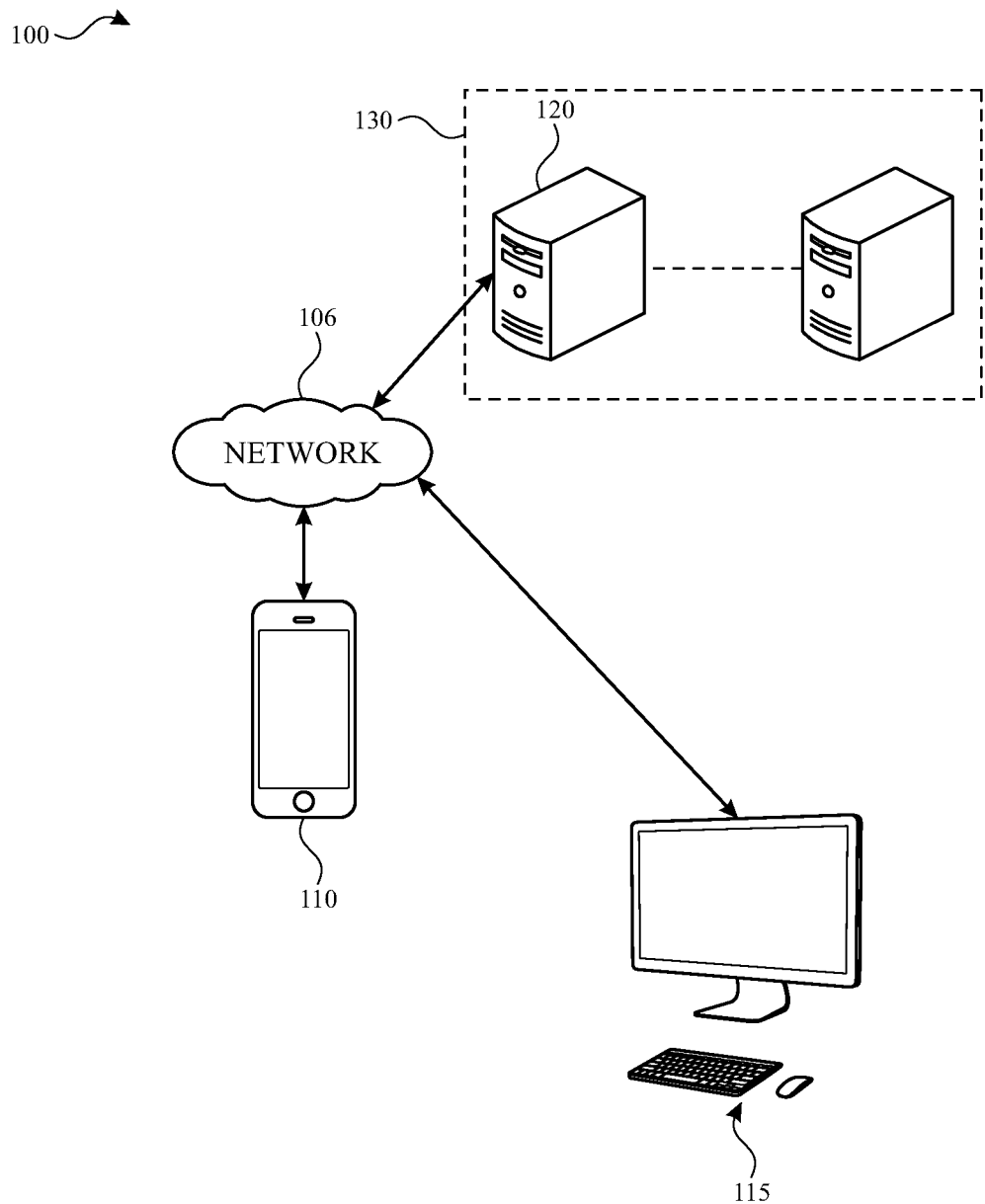
FIG. 1 illustrates an example network architecture in accordance with one or more implementations.

FIG. 1 illustrates an example system architecture 100 including various electronic devices that may implement the subject system in accordance with one or more implementations. Not all of the depicted components may be used in all implementations, however, and one or more implementations may include additional or different components than those shown in the figure. Variations in the arrangement and type of the components may be made without departing from the spirit or scope of the claims as set forth herein. Additional components, different components, or fewer components may be provided.

The system architecture 100 includes an electronic device 110, an electronic device 115, and a server 120. For explanatory purposes, the system architecture 100 is illustrated in FIG. 1 as including the electronic device 110, the electronic device 115, and the server 120; however, the system architecture 100 may include any number of electronic devices, and any number of servers or a data center including multiple servers.

The network 106 may communicatively (directly or indirectly) couple, for example, the electronic device 110, and/or the electronic device 115 with each other device and/or the server 120. In one or more implementations, the network 106 may be an interconnected network of devices that may include, or may be communicatively coupled to, the Internet.

The electronic device 110 may be, for example, a portable computing device such as a laptop computer, a smartphone, a peripheral device (e.g., a digital camera, headphones), a tablet device, a wearable device such as a watch, a band, and the like, or any other appropriate device that includes, for example, one or more wireless interfaces, such as WLAN radios, cellular radios, Bluetooth radios, Zigbee radios, near field communication (NFC) radios, and/or other wireless radios. In FIG. 1, by way of example, the electronic device 110 is depicted as a smartphone. The electronic device 110 may be, and/or may include all or part of the electronic system discussed below with respect to FIG. 7.

The electronic device 115 may be, for example, desktop computer, a portable computing device such as a laptop computer, a smartphone, a peripheral device (e.g., a digital camera, headphones), a tablet device, a wearable device such as a watch, a band, and the like. In FIG. 1, by way of example, the electronic device 115 is depicted as a desktop computer. The electronic device 115 may be, and/or may include all or part of, the electronic system discussed below with respect to FIG. 7.

The server 120 may form all or part of a network of computers or a group of servers 130, such as in a cloud computing or data center implementation. For example, the server 120 stores data and software, and includes specific hardware (e.g., processors, graphics processors and other specialized or custom processors) for generating, storing, and/or providing access to compact, searchable, random-access genome data, including for large datasets such as an entire human genome, and/or verifying and/or authenticating users of the server (e.g., for access to applications and/or data). In an implementation, the server 120 may function as a cloud server. In various examples described herein, the server 120 is described as performing operations for encoding and compressing genome data, and storing and providing access (e.g., by the electronic device 110 and/or the electronic device 115) to the encoded, compressed genome data. However, it is appreciated that other servers, systems, and/or devices (e.g., by the electronic device 110 and/or the electronic device 115) may be used to generate, store, and/or provide access to compact, searchable, random-access genome data.

Figures 2, 3:
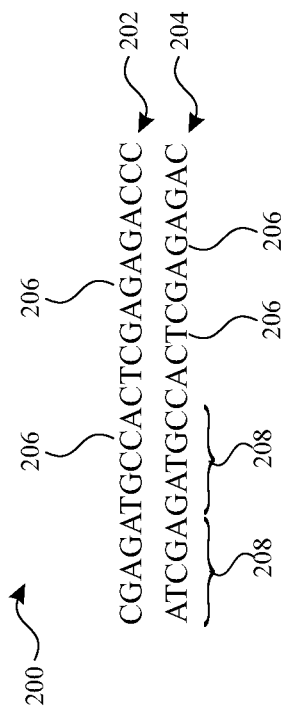
FIG. 2 illustrates an example sequence of genome data that can be encoded in accordance with one or more implementations.
FIG. 3 illustrates various example records including encodings of portions of a sequence of genome data in accordance with one or more implementations.

FIG. 2 illustrates an example of a sequence of genome data 200 that can be encoded and/or compressed using the operations described herein. In the example of FIG. 2, genome data 200 for a diploid cell or organism (e.g., a human) is shown, in which the genome data 200 includes two parallel sequences of nucleotides (e.g., each sequence of the two parallel sequences corresponding to a strand of DNA for a single chromosome of a pair of homologous chromosomes). It is appreciated that a strand of DNA for each allele actually includes a base pair of nucleotides at each location along the sequence. However, since each the nucleotides Adenine (A), Cytosine (C), Guanine (G), and Thymine (T) of DNA can only pair with a single other one of these nucleotides, for simplicity and clarity, only a single one of the nucleotides of each base pair is described herein for a given allele in a sequence of genetic data.

In the example of FIG. 2, the sequence of genome data 200 may include sequence data corresponding to a first allele 202 and a second allele 204. For example, first allele 202 and the second allele 204 represent alternative forms of a single gene, and are located at the same location, respectively, on a first chromosome and a second chromosome of a pair of homologous chromosomes. As shown, the first allele 202 and the second allele 204 are each defined by a sequence of nucleotide symbols 206, corresponding (in this example) to the nucleotides Adenine (A), Cytosine (C), Guanine (G), and Thymine (T). Each location (e.g., locus) along the sequence of genome data 206 has a corresponding nucleotide symbol 206 in each of the first allele 202 and the second allele 204. Each chromosome of a pair of chromosomes of a diploid cell or organism is formed by long chains of nucleotides 206, contiguous sections of which form genes. The various genes on a given chromosome have varying lengths and nucleotide orders, and are each often much longer than the illustrative sequences of nucleotides 206 shown in FIG. 2 for first allele 202 and second allele 204. Groups of nucleotide symbols 206 (e.g., groups corresponding to a gene, or other groups) may be identified by a start location on the sequence for a particular chromosome, and a length of the group along the sequence.

In the example of FIG. 2, the sequence of genome data 200 is represented using the typical eight-bit characters A, C, G, and T to represent the respective nucleotides Adenine, Cytosine, Guanine, and Thymine. However, storing and/or transmitting the billions of nucleotides in an entire human genome (or even substantial or large portions thereof) using these eight-bit characters can be an inefficient usage of computing resources.

One option for reducing the size of stored and/or transmitted genome data is to compress the data using, for example, lossy compression algorithms or compression algorithms such as the Lempel-Ziv (LZ) compression algorithm. However, existing compression algorithms for generic data, if applied to genome data, can result in storage of the compressed data that may prevent the data from being searchable, which can reduce the usefulness of the stored data and/or increase the time, energy, and/or processing resources needed to decode and then query the data. Another option for reducing the size of the stored and/or transmitted genome data is to use the Variant Call Format (VCF) or genome Variant Call Format (gVCF), in which only the differences from a reference genome are stored for a given genome sequence. However, as described in further detail herein, even this VCF data can be more compactly and efficiently stored using the encoding and compression operations described herein, while maintaining the searchability of the stored data.

In accordance with aspects of the disclosure, a sequence of genome data, such as the sequence of genome data 200, may be segmented into records that (i) have a common record length that does not necessarily correlate with the lengths of genes or alleles in the sequence, (ii) each have a record location that corresponds to location along the sequence of the genome data, and (iii) each include information (in the examples of storing diploid data) for both of the alleles at that location along the sequence. Because the record length of a record may be fixed, and may be different from the length of an allele or a gene (which vary from allele to allele and/or from gene to gene), each record may store the entire information for two alleles, or store a subset of the information for two alleles that have a combined encoded length that is longer than the record length. For example, a single record may store all of the information for the first allele 202 and the second allele 204 of FIG. 2, or individual records may only store corresponding segments 208 of the information for the first allele 202 and the second allele 204. In some examples, the information for the first allele 202 and the second allele 204 of FIG. 2 may exactly fill a record. In other examples, the information for the first allele 202 and the second allele 204 of FIG. 2 may fill less than an entire record, which may then be padded with zeros (for example).

For example, a record storing all of the information for the illustrative first allele 202 and the second allele 204 of FIG. 2 (each of which has an allele length of 22 nucleotides) may include a binary string representing the number 22 (for the length of first allele 202), another binary string representing the number 22 (for the length of the second allele 204, which is equal to the length of the first allele 202 in this illustrative example), a binary string representing the actual nucleotides 206 of the first allele 202, and a binary string representing the actual nucleotides 206 of the second allele 204.

As another example, a record storing the information for the leftmost segment 208 of the illustrative first allele 202 and the second allele 204 of FIG. 2 (in which the segment of each allele has an allele length of five nucleotides) may include a binary string representing the number five (for the length of the segment 208 of the first allele 202), another binary string representing the number five (for the length of the segment 208 of the second allele 204, which is equal to the length of the segment 208 first allele 202 in this illustrative example), a binary string representing the actual nucleotides 206 "CGAGA" of the segment 208 of the first allele 202, and a binary string representing the actual nucleotides 206 "ATCGA" of the segment 208 of second allele 204. In this example, the first allele 202 and the second allele 204 would be stored across multiple records. As described in further detail hereinafter, in examples in which data for first and second alleles is stored across multiple records, the record may also include a binary string indicating the number of records across which the data for the first allele 202 and the second allele 204 are stored.

In some implementations described hereinafter, rather than directly encoding all of the nucleotide information in a genetic sequence, records may be used to store variant information for each of two alleles (e.g., variant information that only includes nucleotides of a given allele that are different from the nucleotides of a corresponding allele of a reference genome). The fixed size of the records may be determined to be a size that can store all of the information for a typical string of the data that is variant from the reference data (e.g., a size that can store at least about 95 percent of the variant strings that are, on average over many individual genomes, different from the reference genome).

Examples of the record information that can be stored in a given record are shown in FIG. 3.

For example, FIG. 3 shows how a record 300 may include information indicating a first length 302, information indicating a second length 304, and encoded information 306. For example, record 300 may be one of a set of records for the sequence of genome data 200, each record corresponding to a portion (e.g., a segment, such as a contiguous segment) of the genome data having a particular location (e.g., locus) in the sequence. In the example of FIG. 3, for a particular record, the first length 302 may correspond to a length of at least a portion of a first allele (e.g., first allele 202) that is stored in that record and associated with the particular location for that record, and the second length 304 may correspond to a length of least a portion of a second allele (e.g., second allele 204) that is stored in that record and associated with the particular location for that record.

In the example of FIG. 3, example data for example records 308, 310, 312, 314, and 316 are shown. As illustrated, an example record 308 may include information indicating a first length 302 of one, and information indicating a second length 304 of two. In this example, the first length of one (which may be encoded into the record 308 using the binary string "0001") corresponds to the length of a single nucleotide character, A, for the first allele at the sequence location corresponding to the example record 308. In this example, the second length of two (which may be encoded into the record 308 using the binary string "0010") corresponds to the length of two nucleotide characters, TT, for the second allele at the sequence location corresponding to the example record 308. In one or more implementations, in order to include the information indicating the first length 302 and the information indicating the second length 304 in a record, the information indicating the first length 302 of the first allele data in that record and the information indicating the second length 304 of the second allele data in that record may each be encoded, for example, into four bytes of binary data. The example record 308 also shows how the encoded information 306 may include encoded information 322 (e.g., 00) corresponding to the nucleotide character A of the first allele 318, and encoded information 324 (e.g., 1111) corresponding to the nucleotide characters TT of the second allele 320. Thus, the record 308 may include the binary strings 0001 (indicating a first allele length of one), 0010 (indicating a second allele length of 2), 00 (indicating the nucleotide A), and 1111 (indicating the nucleotides TT). The record 308 may include additional data such as padding bits, binary data indicating a record location or start position, binary data indicating an overall length of the record and/or other data in various implementations.

For example, in one or more implementations, the eight-bit character A may be encoded in binary format as 00, the eight-bit character C may be encoded in binary format as 01, the eight-bit character G may be encoded in binary format as 10, and the eight-bit character T may be encoded in binary format as 11. Accordingly, the encoded information 306 of the example record 308 includes the values 001111, encoding the nucleotide values A, TT for the first and second alleles at the location corresponding to that record. It is also appreciated that genetic data for a haploid cell or organism may also be stored compact searchable records using the operations described herein, but for a single gene (e.g., one of the alleles of the diploid examples described herein). It is also appreciated that, although encoding of the nucleotide values A, C, G, and T for DNA data is described herein as an example, the operations described herein can also be applied for compact searchable storage of ribonucleic acid (RNA) data (e.g., by encoding the eight-bit character A in binary format as 00, the eight-bit character C in binary format as 01, the eight-bit character G in binary format as 10, and the eight-bit character U (for Uracil) in binary format as 11, and proceeding as described hereinafter).

Storing the allele lengths (or a single gene length for haploid data) may help maintain searchability of the encoded information in each record, by identifying which of the binary characters in the encoded information 306 of each record correspond to which allele at that location. In one or more implementations, the encoded information 306 corresponding to at least the portion of the first allele can be generated by encoding each nucleotide symbol of at least the portion of the first allele using two bits of binary data, and the encoded information 306 corresponding to at least the portion of the second allele by encoding each nucleotide symbol of at least the portion of the second allele using two bits of binary data.

FIG. 3 also illustrates how each record may be padded (e.g., with additional zeros) if the encoded information for the two alleles at that location in the sequence do not fill the record. In one or more implementations, each record 300 may also include an overall record length that indicates the length of the stored sequence for both alleles in that record (e.g., which may be less than the maximum length of a sequence that can be stored in a single record). The overall record length, the stored first length 302, and the second length 304 can be used, for example, to distinguish between padding values and encoded genetic information for each allele. Each record 300 may also include a start position of the particular location in the sequence for the corresponding portion of the genome data for that record. In this way, any portion of the sequence of genome data that is stored in the records 300 can be located and obtained, by querying the location in the sequence. The data records for that location can then be identified using the start position and the overall record length, the stored first length 302, and the second length 304 of the records 300. In one or more implementations, a record 300 may also include a sequence identifier that identifies the obtained input sequence (e.g., the sequence of genome data 200) for which a particular set of records has been generated. The sequence identifier may identify the sequence, but may not be linked to any particular user or user identifier in cases in which a user has not specifically requested and authorized storage of their own genome data in connection with their own identity. In this way, a database of compact, searchable genome data including genome data for multiple individuals may be provided (i.e., and securely stored after obtaining consent and permission of the individuals, such as in a request from the individuals to store the data and in accordance with any privacy preserving precautions requested by the user and/or required by policy). In one or more implementations, a record 300 may also include a chromosome identifier that identifies the chromosome to which a data in a given record belongs. In one or more implementations each record 300 may have a maximum record length of, for example, ten bytes.

In the example of FIG. 3, an example record 310 includes information indicating a first length 302 of four (e.g., which may be encoded into a binary string 0100 in the record 310) corresponding to the length of a sequence ACGT, and information indicating a second length 304 of seven (e.g., which may be encoded into a binary string 0111 in the record 310), corresponding to the length a sequence CGTACGT. The example records 308 and 310 are examples of records for heterozygous alleles. FIG. 3 also includes an example record 312 for alleles in which the sequence for the data of one allele in the record is the same as a prefix for the data of another allele in the record. In this example, the example record 312 includes a first length 302 of five corresponding to a sequence AAAAA, and a second length 304 of 12, corresponding to a sequence AAAAATTTTTCC, in which the sequence AAAAA is the same as the prefix AAAAA of the second allele. In this example, the binary information for the sequence AAAAA can be stored a single time in the record, and the information indicating the lengths of five and twelve (e.g., and an overall length of the encoded data in that record, such as an overall length of twelve) can indicate that the portions of the encoded information for the first and second alleles are stored in partially overlapping record bits. In this way, the encoding of alleles in which the sequence for one allele is the same as a prefix for another allele can provide an additional compression efficiency for the encoded data.

FIG. 3 also includes an example record 314 for homozygous alleles. In this example, the example record 314 includes information indicating a first length 302 of zero (e.g., to indicate that the alleles are homozygous), and information indicating a second length 304 of three, corresponding to a sequence AGC for both alleles. In this example, the binary information for the sequence AGC can be stored a single time in the record, and the information indicating allele lengths of zero and three can indicate that the portions of the encoded information for the three nucleotides of the first and second alleles are stored in six overlapping record bits (e.g., 001001). In this way, the encoding of homozygous alleles can provide an additional compression efficiency for the encoded data.

FIG. 3 also includes an example record 316 for encoding a portion of a sequence that is too long to be encoded in a single record 300. In the example record 316, the allele lengths for both alleles are fifteen, which may be too long for inclusion in a single record 300 (e.g., record 316 having 24 bits available for encoded nucleotide information). In the example of record 316, the thirty nucleotides (e.g., fifteen each for the first and second alleles), may be partially stored in the record 316 (e.g., in the first half of the sequence data 300), and may be partially stored as overflow data in a series of adjacent records 300, with the total number of overflow records indicated by the number stored in the sequence data 306 (e.g., three total records including two overflow records as indicated by the binary string "11" in the second half of the sequence data 306 of the record 316).

In one or more implementations, the storage overhead may be further reduced (e.g., at a slight cost of query performance) by bundling sets of the records 300 into a single larger record, as described in further detail hereinafter. Once the records 300 (e.g., including records such as the example records 308, 310, 312, 314, and 316) are generated (e.g., and bundled, in one or more implementations), the records can be stored in a database (e.g., a tree data structure, such as a B-tree, or a B+ tree) as a compressed searchable random-access version of the sequence of genome data.

As described herein, the encoding and compression operations described herein for generating the records 300 can be applied to VCF data, to achieve further data compression and storage efficiencies. For example, a sequence of genome data 200 may be obtained as a sequence of Variant Call Format (VCF) data, as shown in FIG. 4.

Figure 4:
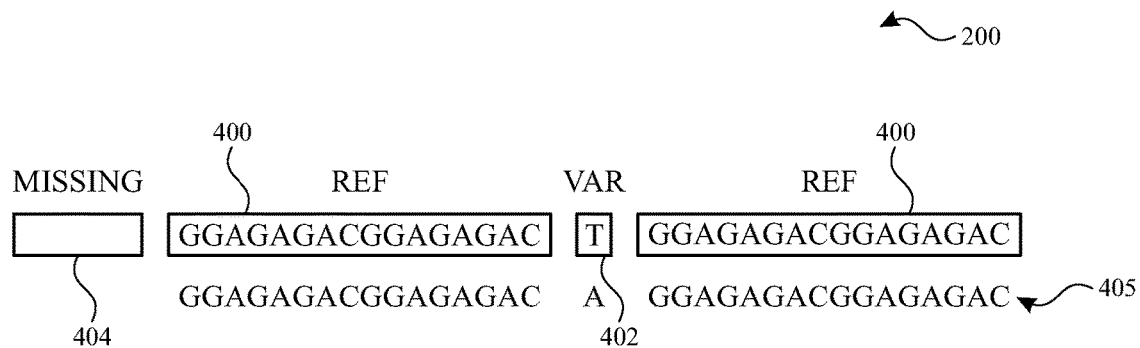
FIG. 4 illustrates an example sequence of genome data in a Variant Call Format (VCF) in accordance with one or more implementations.

As shown in FIG. 4, the sequence of VCF data may include reference records 400 that include genome data that are the same as a reference genome 405, variant records 402 that include genome data that differs from the reference genome 405, and/or missing records 404 that are missing from the sequence of genome data.

In one or more implementations, the nucleotide characters in the variant records 402 of the sequence of VCF data may be encoded into records 300, as described above in connection with FIG. 3. In one or more implementations, the reference records may be encoded into additional records that do not include genetic information, but indicate that the genome data for that record is the same as the reference genome at the same location.

For example, additional records may also be generated for the reference records 400 of input VCF data. These additional records may also each correspond to a respective portion of the genome data having a respective particular location in the sequence. Each additional record for the reference records 400 may include a start position of the particular location in the sequence for the corresponding reference record 400, and a single length of the corresponding portion of the genome data for that reference record (e.g., the records may be similar to the records 300 described above, but without including two allele lengths, and without including encoded genetic information). In this way, the records generated herein for the reference records 400 of VCF data may remain free of genome information. In one or more implementations, a single record may be stored for each non-overlapping interval of reference-matching data in the input sequence (e.g., up to a size limit of, for example, 65535, beyond which an interval may be split into multiple records).

In one or more implementations, variant records 402 may be encoded into records 300 that have a length of ten bytes. For example, it has been determined by the subject technology that, as much as about 95% of variant records 402 can be encoded into records 300 of ten byte length.

In one or more implementations, the reference records 400 may be encoded into records having a length of six bytes (e.g., smaller than the records that encode the variant records 402, due to the lack of encoded genetic information for the reference records). In one or more implementations, the reference genome for the VCF data may also be stored, unencoded, or encoded and compressed (e.g., into a set of records 300 using the encoding and compression operations described herein).

Figure 5:
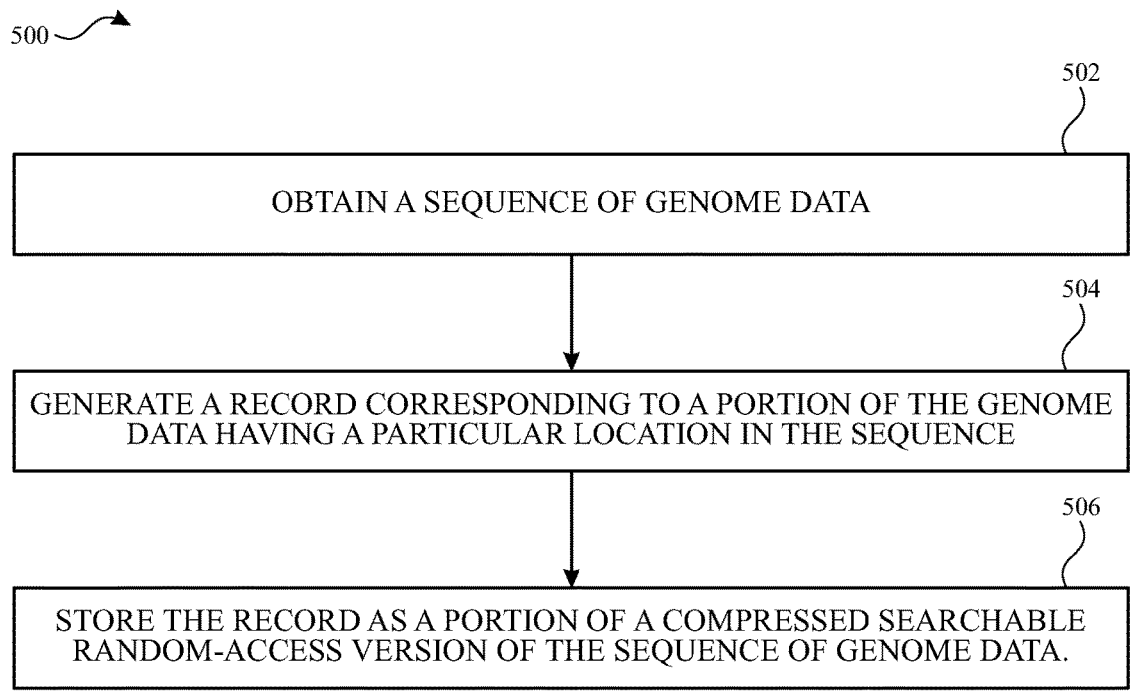
FIG. 5 illustrates a flow diagram of an example process for compressing and encoding genome data in accordance with one or more implementations.

FIG. 5 illustrates a flow diagram of an example process for encoding and storing genome data, in accordance with one or more implementations. For explanatory purposes, the process 500 is primarily described herein with reference to the electronic device 110 and server 120 of FIG. 1. However, the process 500 is not limited to the electronic device 110 and server 120 of FIG. 1, and one or more blocks (or operations) of the process 500 may be performed by one or more other components of the server 120 or the electronic device 110 and/or by other suitable devices such as electronic device 115. Further for explanatory purposes, the blocks of the process 500 are described herein as occurring in series, or linearly. However, multiple blocks of the process 500 may occur in parallel. In addition, the blocks of the process 500 need not be performed in the order shown and/or one or more blocks of the process 500 need not be performed and/or can be replaced by other operations.

At block 502, a computing system (e.g., an electronic device or a server) may obtain a sequence of genome data, such as the sequence of genome data 200 of FIG. 2. In one or more implementations, the sequence of genome data corresponds to an entire human genome or a human exome.

At block 504, the computing system may generate a record (e.g., record 300) corresponding to a portion of the genome data having a particular location in the sequence. The record may include a first length (e.g., first length 302) corresponding to at least a portion of a first allele associated with the particular location. The record may also include a second length (e.g., second length 304) corresponding to a least a portion of a second allele associated with the particular location. In one or more implementations, the record may include the first length and the second length by including first (e.g., binary) encoded information indicating the first length and second encoded (e.g., binary) information indicating the second length. The record may also include first encoded information (e.g., encoded information 322) corresponding to at least the portion of the first allele. The record may also include second encoded information (e.g., encoded information 324) corresponding to at least the portion of the second allele.

For example, the sequence of genome data may include a sequence of nucleotide symbols (e.g., nucleotide symbols 206). In one or more implementations, the computing system may generate the first encoded information corresponding to at least the portion of the first allele by encoding each nucleotide symbol of at least the portion of the first allele using two bits of binary data. In one or more implementations, the computing system may generate the second encoded information corresponding to at least the portion of the second allele by encoding each nucleotide symbol of at least the portion of the second allele using two bits of binary data.

In one or more implementations, the record may also include a start position of the particular location in the sequence for the corresponding portion of the genome data.

In one or more implementations, generating the record may include determining that the at least the portion of the first allele is a prefix for the at least the portion of the second allele, and setting at least one of the first length or the second length (e.g., and/or an overall length) for the record to indicate an overlap, in the record, of the first encoded information corresponding to at least the portion of the first allele and the second encoded information corresponding to at least the portion of the second allele.

In one or more implementations, generating the record may include determining that the at least the portion of the first allele and the at least the portion of the second allele are homozygous, and setting the first length or the second length for the record to zero.

At block 506, the computing system may store the record (e.g., in a database) as a portion of a compressed searchable random-access version of the sequence of genome data.

In one or more implementations, the computing system may also generate a plurality of additional records (e.g., additional records 300), each additional record corresponding to an additional respective portion of the genome data having an additional respective particular location in the sequence. Each additional record may include a respective first length corresponding to at least a respective portion of a respective first allele associated with the additional respective particular location. Each additional record may also include a respective second length corresponding to a least a respective portion of a respective second allele associated with the additional respective particular location. Each additional record may also include respective first encoded information corresponding to at least the respective portion of the respective first allele. Each additional record may also include respective second encoded information corresponding to at least the respective portion of the respective second allele. The computing system may also store the plurality of additional records in the compressed searchable random-access version of the sequence of genome data. For example, the additional records may be generated for all additional portions of the genome data (e.g., or all portions of the genome data that vary from a reference genome) until all of the genome data (e.g., or all of the genome data that vary from the reference genome) has been encoded and stored in a set of the records.

In one or more implementations, each of the plurality of additional records further includes a respective start position of the additional respective particular location in the sequence for the additional respective portion of the genome data. In one or more implementations, the computing system may also, prior to storing the plurality of additional records, bundle at least one group of the plurality of additional records to form a bundle.

For example, the computing system may bundle at least one group of the plurality of additional records to form a bundle by setting a bundle start position for the bundle to the start position of a first record of the at least one group, and replacing the start position of each record of the at least one group with an offset from the bundle start position. In one or more implementations, some or all of the remaining records may also be bundled and stored to form the compressed searchable random-access version of the sequence of genome data.

In one or more implementations, the plurality of additional records may be a first plurality of first records. In one or more implementations, the computing system may also generate a second plurality of second records, each second record corresponding to a portion of the genome data having a particular location in the sequence. Each second record may include a start position of the particular location in the sequence for the corresponding portion of the genome data for that second record, and a single length of the corresponding portion of the genome data for that second record. Each second record may be free of genome information.

For example, in one or more implementations, the sequence of genome data may be a sequence of Variant Call Format (VCF) data. For example, each of the first records may correspond to a variant record (e.g., a variant record 402) in the sequence of VCF data, and each of the second records may correspond to a reference record (e.g., a reference record 400) in the sequence of VCF data. In one or more implementations, the sequence of VCF data may include at least one missing record (e.g., a missing record 404) having a corresponding location in the sequence. The compressed searchable random-access version of the genome data may be free of data corresponding to the at least one missing record.

The compressed searchable random-access version of the genome data may be stored in a database that is accessible and/or searchable (e.g., by authorized users).

Figure 6:
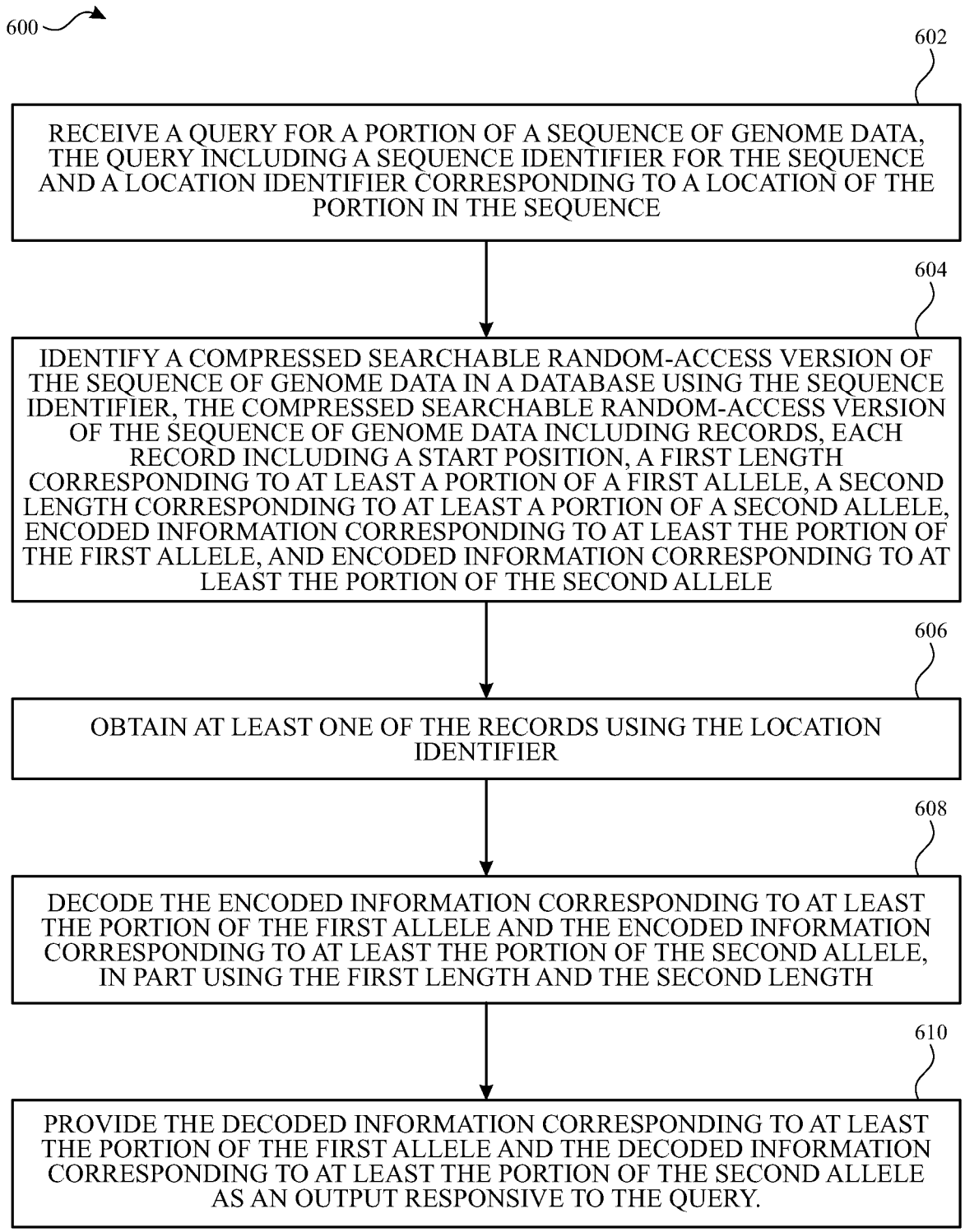
FIG. 6 illustrates a flow diagram of an example process for accessing compressed encoded genome data in accordance with one or more implementations.

FIG. 6 illustrates a flow diagram of an example process for providing access to encoded genome data, in accordance with one or more implementations. For explanatory purposes, the process 600 is primarily described herein with reference to the electronic device 110 and server 120 of FIG. 1. However, the process 600 is not limited to the electronic device 110 and server 120 of FIG. 1, and one or more blocks (or operations) of the process 600 may be performed by one or more other components of the server 120 or the electronic device 110 and/or by other suitable devices such as electronic device 115. Further for explanatory purposes, the blocks of the process 600 are described herein as occurring in series, or linearly. However, multiple blocks of the process 600 may occur in parallel. In addition, the blocks of the process 600 need not be performed in the order shown and/or one or more blocks of the process 600 need not be performed and/or can be replaced by other operations.

At block 602, a query for a portion of a sequence of genome data may be received (e.g., at a server or other electronic device storing compressed searchable random-access versions of the sequences of genome data generated using one or more aspects of the process described above in connection with FIG. 5). The query may include a sequence identifier for the sequence and a location identifier corresponding to a location of the portion in the sequence. In one or more implementations, the sequence of genome data may include an entire human genome, a human exome, one or more portions thereof, or other genome data. In various implementations, a query may be query for genome data of a particular individual (e.g., an individual identified by an anonymous identifier that is unrelated to personal details of the individual such as the individuals name or contact information, or a personal identifier if explicit permission and an express request for storage of personal genome data has been received from the individual). In various implementations, a query may be a query for a particular gene, a particular chromosome, or a particular nucleotide sequence (as examples), such as for medical evaluation purposes, generalized medical research purposes, family history evaluation purposes, and/or family tree evaluation purposes for the individual or individuals to which the genome data corresponds and/or for other authorized users of the genome data.

At block 604, a compressed searchable random-access version of the sequence of genome data may be identified (e.g., by the server or other electronic device) in a database using the sequence identifier. The compressed searchable random-access version of the sequence of genome data may include a plurality of records (e.g., including records 300), each record including a start position, a first length corresponding to at least a portion of a first allele, a second length corresponding to a least a portion of a second allele, encoded information corresponding to at least the portion of the first allele, and encoded information corresponding to at least the portion of the second allele. The compressed searchable random-access version of the sequence of genome data may also include an additional plurality of records that each include a start position of the particular location in the sequence for the corresponding portion of the genome data for that additional record, a single length of the corresponding portion of the genome data for that additional record, that are each free of genome information.

At block 606, at least one of the records may be obtained (e.g., by the server) using the location identifier. For example, the location identifier may be mapped to a location identifier in the at least one of the records. The at least one of the records corresponding to the location identifier in the at least one of the records may be obtained.

At block 608, the encoded information in the obtained record corresponding to at least the portion of the first allele and the encoded information corresponding to at least the portion of the second allele may be decoded (e.g., by the server), in part using the first length and the second length.

In one or more implementations, decoding the encoded information corresponding to at least the portion of the first allele and the encoded information corresponding to at least the portion of the second allele, in part using the first length and the second length, may include obtaining a first set of binary data (e.g., encoded information 322) having a length (e.g., first length 302) corresponding to the first length from the record and obtaining a second set of binary data (e.g., encoded information 324) having a length (e.g., second length 304) corresponding to the second length from the record. The first set of binary data may be converted to one or more nucleotide characters (e.g., nucleotide symbols 206) for the first allele, and the second set of binary data may be converted to one or more nucleotide characters (e.g., nucleotide symbols 206) for the second allele.

At block 610, the decoded information corresponding to at least the portion of the first allele and the decoded information corresponding to at least the portion of the second allele may be provided (e.g., by the server) as an output responsive to the query.

In one or more implementations, the encoding and compression operations described herein can provide a genome database that can store and manage multiple genome datasets efficiently, and serve as a unified data backend for a variety of genome input file formats including, for example, VCF and gVCF. In one or more implementations, a human genome initially obtained in a VCF format and having a size of approximately 200 MB to 250 MB can be stored in records 300, with a reduced total size of approximately 40 MB to 50 MB or less. In one or more implementations, a human genome initially obtained in a gVCF format and having a size of approximately 6 GB to 7 GB can be stored in records 300, with a reduced total size of approximately 90 MB to 95 MB or less. In one or more implementations, a human exome initially obtained in a gVCF format and having a size of approximately 1 GB to 2 GB can be stored in records 300, with a reduced total size of approximately 35 MB to 45 MB or less.

As described above, one aspect of the present technology is the gathering and use of data available from various sources to encode, compress and/or store the data. The present disclosure contemplates that in some instances, this gathered data may include personal information data that uniquely identifies or can be used to contact or locate a specific person. Such personal information data can include demographic data, location-based data, telephone numbers, email addresses, twitter IDs, home addresses, data or records relating to a user's health or level of fitness (e.g., genetic data such as genome data, DNA data, RNA data, vital signs measurements, medication information, exercise information), date of birth, or any other identifying or personal information.

The present disclosure recognizes that the use of such personal information data, in the present technology, can be used to the benefit of users. For example, the personal information data can be used to provide a person with access to their own stored genome data and/or to provide access to others explicitly authorized by the person to access the stored genome data or for legitimate medical research using explicitly authorized access to de-identified genetic data of multiple persons. Accordingly, use of such personal information data enables users to review and/or learn about their own genetics. Further, other uses for personal information data that benefit the user are also contemplated by the present disclosure. For instance, stored, searchable genome data can enable users to obtain targeted medical care based on their genetic information.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of encoding, compressing, and/or storing genome data, the present technology can be configured to allow users to select to "opt in" or "opt out" of participation in the collection of personal information data during registration for services or anytime thereafter. In another example, users can select not to provide genetic data for storage or not to provide personally identifying information that links an individual to any specific genetic data. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data at a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, genome data may be stored with an identifier that is based on non-personal information data or a bare minimum amount of personal information, such as personal information provided and explicitly authorized by the informed user specifically for association with the genetic data.

Figure 7:
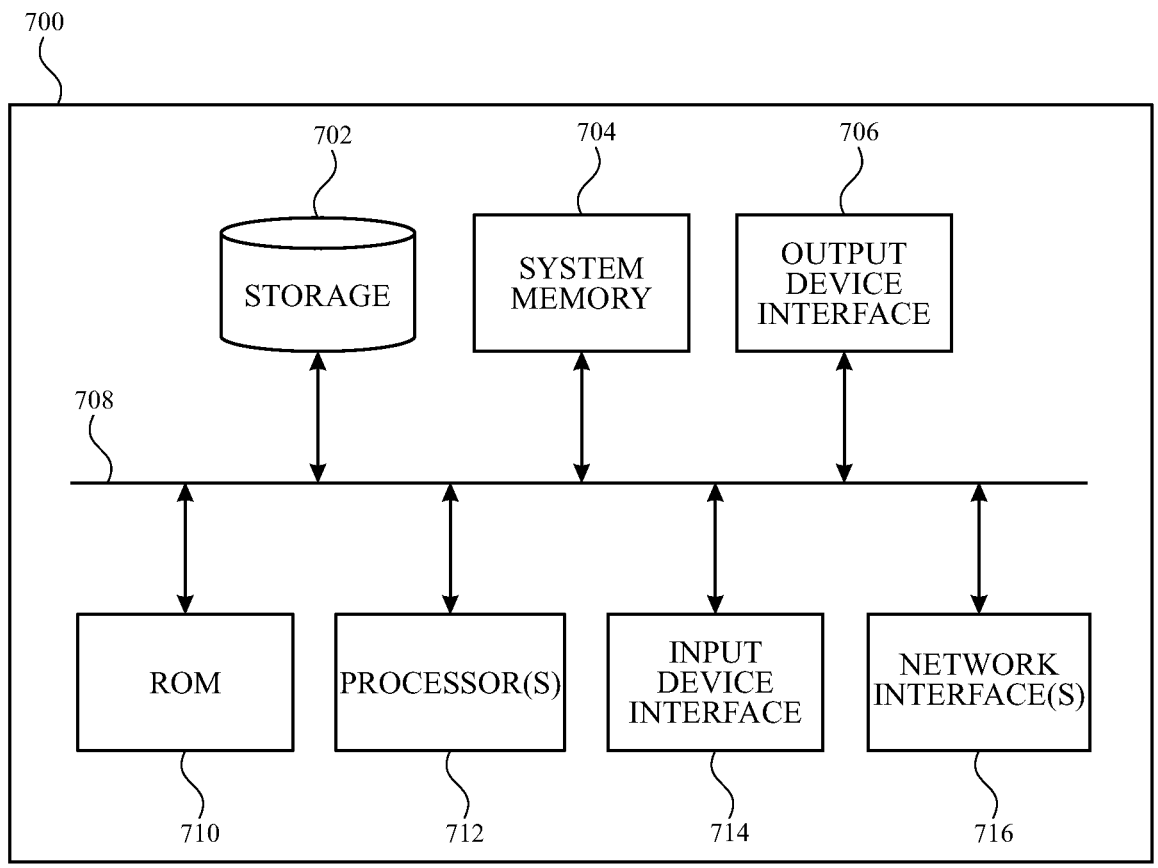
FIG. 7 illustrates an electronic system with which one or more implementations of the subject technology may be implemented.

FIG. 7 illustrates an electronic system 700 with which one or more implementations of the subject technology may be implemented. The electronic system 700 can be, and/or can be a part of, the electronic device 110, and/or the server 120 shown in FIG. 1. The electronic system 700 may include various types of computer readable media and interfaces for various other types of computer readable media. The electronic system 700 includes a bus 708, one or more processing unit(s) 712, a system memory 704 (and/or buffer), a ROM 710, a permanent storage device 702, an input device interface 714, an output device interface 706, and one or more network interfaces 716, or subsets and variations thereof.

The bus 708 collectively represents all system, peripheral, and chipset buses that communicatively connect the numerous internal devices of the electronic system 700. In one or more implementations, the bus 708 communicatively connects the one or more processing unit(s) 712 with the ROM 710, the system memory 704, and the permanent storage device 702. From these various memory units, the one or more processing unit(s) 712 retrieves instructions to execute and data to process in order to execute the processes of the subject disclosure. The one or more processing unit(s) 712 can be a single processor or a multi-core processor in different implementations.

The ROM 710 stores static data and instructions that are needed by the one or more processing unit(s) 712 and other modules of the electronic system 700. The permanent storage device 702, on the other hand, may be a read-and-write memory device. The permanent storage device 702 may be a non-volatile memory unit that stores instructions and data even when the electronic system 700 is off. In one or more implementations, a mass-storage device (such as a magnetic or optical disk and its corresponding disk drive) may be used as the permanent storage device 702.

In one or more implementations, a removable storage device (such as a floppy disk, flash drive, and its corresponding disk drive) may be used as the permanent storage device 702. Like the permanent storage device 702, the system memory 704 may be a read-and-write memory device. However, unlike the permanent storage device 702, the system memory 704 may be a volatile read-and-write memory, such as random access memory. The system memory 704 may store any of the instructions and data that one or more processing unit(s) 712 may need at runtime. In one or more implementations, the processes of the subject disclosure are stored in the system memory 704, the permanent storage device 702, and/or the ROM 710. From these various memory units, the one or more processing unit(s) 712 retrieves instructions to execute and data to process in order to execute the processes of one or more implementations.

The bus 708 also connects to the input and output device interfaces 714 and 706. The input device interface 714 enables a user to communicate information and select commands to the electronic system 700. Input devices that may be used with the input device interface 714 may include, for example, alphanumeric keyboards and pointing devices (also called "cursor control devices"). The output device interface 706 may enable, for example, the display of images generated by electronic system 700. Output devices that may be used with the output device interface 706 may include, for example, printers and display devices, such as a liquid crystal display (LCD), a light emitting diode (LED) display, an organic light emitting diode (OLED) display, a flexible display, a flat panel display, a solid state display, a projector, or any other device for outputting information. One or more implementations may include devices that function as both input and output devices, such as a touchscreen. In these implementations, feedback provided to the user can be any form of sensory feedback, such as visual feedback, auditory feedback, or tactile feedback; and input from the user can be received in any form, including acoustic, speech, or tactile input.

Finally, as shown in FIG. 7, the bus 708 also couples the electronic system 700 to one or more networks and/or to one or more network nodes, such as the electronic device 110 shown in FIG. 1, through the one or more network interface(s) 716. In this manner, the electronic system 700 can be a part of a network of computers (such as a LAN, a wide area network ("WAN"), or an Intranet, or a network of networks, such as the Internet. Any or all components of the electronic system 700 can be used in conjunction with the subject disclosure.

In accordance with aspects of the disclosure, a method is provided that includes obtaining a sequence of genome data; generating a record corresponding to a portion of the genome data having a particular location in the sequence, the record including: a first length corresponding to at least a portion of a first allele associated with the particular location, a second length corresponding to a least a portion of a second allele associated with the particular location, first encoded information corresponding to at least the portion of the first allele, and second encoded information corresponding to at least the portion of the second allele. The method also includes storing the record as a portion of a compressed searchable random-access version of the sequence of genome data.

In accordance with aspects of the disclosure, a method is provided that includes receiving a query for a portion of a sequence of genome data, the query including a sequence identifier for the sequence and a location identifier corresponding to a location of the portion in the sequence. The method also includes identifying a compressed searchable random-access version of the sequence of genome data in a database using the sequence identifier. The compressed searchable random-access version of the sequence of genome data includes a plurality of records, each record including a start position, a first length corresponding to at least a portion of a first allele, a second length corresponding to a least a portion of a second allele, encoded information corresponding to at least the portion of the first allele, and encoded information corresponding to at least the portion of the second allele. The method also includes obtaining at least one of the records using the location identifier. The method also includes decoding the encoded information corresponding to at least the portion of the first allele and the encoded information corresponding to at least the portion of the second allele, in part using the first length and the second length. The method also includes providing the decoded information corresponding to at least the portion of the first allele and the decoded information corresponding to at least the portion of the second allele as an output responsive to the query.

In accordance with aspects of the disclosure, a non-transitory machine-readable medium is provided that stored instructions which, when executed by a processor, cause the processor to obtain a sequence of genome data; generate a record corresponding to a portion of the genome data having a particular location in the sequence, the record including: a first length corresponding to at least a portion of a first allele associated with the particular location, a second length corresponding to a least a portion of a second allele associated with the particular location, encoded information corresponding to at least the portion of the first allele, and encoded information corresponding to at least the portion of the second allele; and storing the record as a compressed searchable random-access version of the sequence of genome data.

Implementations within the scope of the present disclosure can be partially or entirely realized using a tangible computer-readable storage medium (or multiple tangible computer-readable storage media of one or more types) encoding one or more instructions. The tangible computer-readable storage medium also can be non-transitory in nature.

The computer-readable storage medium can be any storage medium that can be read, written, or otherwise accessed by a general purpose or special purpose computing device, including any processing electronics and/or processing circuitry capable of executing instructions. For example, without limitation, the computer-readable medium can include any volatile semiconductor memory, such as RAM, DRAM, SRAM, T-RAM, Z-RAM, and TTRAM. The computer-readable medium also can include any non-volatile semiconductor memory, such as ROM, PROM, EPROM, EEPROM, NVRAM, flash, nvSRAM, FeRAM, FeTRAM, MRAM, PRAM, CBRAM, SONOS, RRAM, NRAM, racetrack memory, FJG, and Millipede memory.

Further, the computer-readable storage medium can include any non-semiconductor memory, such as optical disk storage, magnetic disk storage, magnetic tape, other magnetic storage devices, or any other medium capable of storing one or more instructions. In one or more implementations, the tangible computer-readable storage medium can be directly coupled to a computing device, while in other implementations, the tangible computer-readable storage medium can be indirectly coupled to a computing device, e.g., via one or more wired connections, one or more wireless connections, or any combination thereof.

Instructions can be directly executable or can be used to develop executable instructions. For example, instructions can be realized as executable or non-executable machine code or as instructions in a high-level language that can be compiled to produce executable or non-executable machine code. Further, instructions also can be realized as or can include data. Computer-executable instructions also can be organized in any format, including routines, subroutines, programs, data structures, objects, modules, applications, applets, functions, etc. As recognized by those of skill in the art, details including, but not limited to, the number, structure, sequence, and organization of instructions can vary significantly without varying the underlying logic, function, processing, and output.

While the above discussion primarily refers to microprocessor or multi-core processors that execute software, one or more implementations are performed by one or more integrated circuits, such as ASICs or FPGAs. In one or more implementations, such integrated circuits execute instructions that are stored on the circuit itself.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application. Various components and blocks may be arranged differently (e.g., arranged in a different order, or partitioned in a different way) all without departing from the scope of the subject technology.

It is understood that any specific order or hierarchy of blocks in the processes disclosed is an illustration of example approaches. Based upon design preferences, it is understood that the specific order or hierarchy of blocks in the processes may be rearranged, or that all illustrated blocks be performed. Any of the blocks may be performed simultaneously. In one or more implementations, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

As used in this specification and any claims of this application, the terms "base station", "receiver", "computer", "server", "processor", and "memory" all refer to electronic or other technological devices. These terms exclude people or groups of people. For the purposes of the specification, the terms "display" or "displaying" means displaying on an electronic device.

As used herein, the phrase "at least one of preceding a series of items, with the term "and" or "or" to separate any of the items, modifies the list as a whole, rather than each member of the list (i.e., each item). The phrase "at least one of does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The predicate words "configured to", "operable to", and "programmed to" do not imply any particular tangible or intangible modification of a subject, but, rather, are intended to be used interchangeably. In one or more implementations, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

Phrases such as an aspect, the aspect, another aspect, some aspects, one or more aspects, an implementation, the implementation, another implementation, some implementations, one or more implementations, an embodiment, the embodiment, another embodiment, some implementations, one or more implementations, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

The word "exemplary" is used herein to mean "serving as an example, instance, or illustration". Any embodiment described herein as "exemplary" or as an "example" is not necessarily to be construed as preferred or advantageous over other implementations. Furthermore, to the extent that the term "include", "have", or the like is used in the description or the claims, such term is intended to be inclusive in a manner similar to the term "comprise" as "comprise" is interpreted when employed as a transitional word in a claim.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "step for".

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language claims, wherein reference to an element in the singular is not intended to mean "one and only one" unless specifically so stated, but rather "one or more". Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the subject disclosure.

What is claimed is:

1. A method, comprising:
   obtaining a sequence of genome data;
   generating a record corresponding to a portion of the genome data having a particular location in the sequence, the record including:
   a first length corresponding to at least a portion of a first allele associated with the particular location,
   a second length corresponding to at least a portion of a second allele associated with the particular location,
   first encoded information corresponding to at least the portion of the first allele, and
   second encoded information corresponding to at least the portion of the second allele; and
   storing the record as a portion of a compressed searchable random-access version of the sequence of genome data.

2. The method of claim 1, wherein the sequence of genome data comprises a sequence of nucleotide symbols, the method further comprising:
   generating the first encoded information corresponding to at least the portion of the first allele by encoding each nucleotide symbol of at least the portion of the first allele using two bits of binary data; and
   generating the second encoded information corresponding to at least the portion of the second allele by encoding each nucleotide symbol of at least the portion of the second allele using two bits of binary data.

3. The method of claim 1, wherein the record further includes a start position of the particular location in the sequence for the corresponding portion of the genome data.

4. The method of claim 1, wherein generating record further comprises:
   determining that the at least the portion of the first allele is a prefix for the at least the portion of the second allele; and
   setting at least one of the first length or the second length for the record to indicate an overlap, in the record, of the first encoded information corresponding to at least the portion of the first allele and the second encoded information corresponding to at least the portion of the second allele.

5. The method of claim 1, wherein generating the record further comprises: determining that the at least the portion of the first allele and the at least the portion of the second allele are homozygous; and
   setting the first length or the second length for the record to zero.

6. The method of claim 1, further comprising:
   generating a plurality of additional records, each additional record corresponding to an additional respective portion of the genome data having an additional respective particular location in the sequence, each additional record comprising:
   a respective first length corresponding to at least a respective portion of a respective first allele associated with the additional respective particular location,
   a respective second length corresponding to at least a respective portion of a respective second allele associated with the additional respective particular location,
   respective first encoded information corresponding to at least the respective portion of the respective first allele, and
   respective second encoded information corresponding to at least the respective portion of the respective second allele; and
   storing the plurality of additional records in the compressed searchable random-access version of the sequence of genome data.

7. The method of claim 6, wherein the each of the plurality of additional records further includes a respective start position of the additional respective particular location in the sequence for the additional respective portion of the genome data, the method further comprising:
   prior to storing the plurality of additional records, bundling at least one group of the plurality of additional records to form a bundle, by:
   setting a bundle start position for the bundle to the start position of a first record of the at least one group; and
   replacing the start position of each record of the at least one group with an offset from the bundle start position.

8. The method of claim 6, wherein the plurality of additional records comprises a first plurality of first records, and wherein the method further comprises:
   generating a second plurality of second records, each second record corresponding to a portion of the genome data having a particular location in the sequence, and each second record including:
   a start position of the particular location in the sequence for the corresponding portion of the genome data for that second record; and
   a single length of the corresponding portion of the genome data for that second record.

9. The method of claim 8, wherein each second record is free of genome information.

10. The method of claim 8, wherein the sequence of genome data comprises a sequence of Variant Call Format (VCF) data, wherein each of the first records corresponds to a variant record in the sequence of VCF data, and each of the second records corresponds to a reference record in the sequence of VCF data.

11. The method of claim 10, wherein the sequence of VCF data includes at least one missing record having a corresponding location in the sequence, and wherein the compressed searchable random-access version of the genome data is free of data corresponding to the at least one missing record.

12. The method of claim 1, wherein the sequence of genome data corresponds to an entire human genome.

13. A method, comprising:
    receiving a query for a portion of a sequence of genome data, the query including a sequence identifier for the sequence and a location identifier corresponding to a location of the portion in the sequence;
    identifying a compressed searchable random-access version of the sequence of genome data in a database using the sequence identifier, wherein the compressed searchable random-access version of the sequence of genome data comprises a plurality of records, each record including a start position, a first length corresponding to at least a portion of a first allele, a second length corresponding to at least a portion of a second allele, encoded information corresponding to at least the portion of the first allele, and encoded information corresponding to at least the portion of the second allele;
    obtaining at least one of the records using the location identifier;
    decoding the encoded information corresponding to at least the portion of the first allele and the encoded information corresponding to at least the portion of the second allele, in part using the first length and the second length; and providing the decoded information corresponding to at least the portion of the first allele and the decoded information corresponding to at least the portion of the second allele as an output responsive to the query.

14. The method of claim 13, wherein the sequence of genome data comprises an entire human genome or a human exome.

15. The method of claim 14, wherein decoding the encoded information corresponding to at least the portion of the first allele and the encoded information corresponding to at least the portion of the second allele, in part using the first length and the second length, comprises:
 obtaining a first set of binary data having a length corresponding to the first length from the record;
 obtaining a second set of binary data having a length corresponding to the second length from the record;
 converting the first set of binary data to one or more nucleotide characters for the first allele; and
 converting the second set of binary data to one or more nucleotide characters for the second allele.

16. A non-transitory machine-readable medium storing instructions which, when executed by one or more processors, cause the one or more processors to:
 obtain a sequence of genome data;
 generate a record corresponding to a portion of the genome data having a particular location in the sequence, the record including:
  a first length corresponding to at least a portion of a first allele associated with the particular location,
  a second length corresponding to at least a portion of a second allele associated with the particular location,
  encoded information corresponding to at least the portion of the first allele,
  and encoded information corresponding to at least the portion of the second allele;
 and storing the record as a compressed searchable random-access version of the sequence of genome data.

17. The non-transitory machine-readable medium of claim 16, wherein the sequence of genome data comprises a sequence of nucleotide symbols, and wherein the instructions, when executed by the one or more processors, further cause the one or more processors to:
 generate the encoded information corresponding to at least the portion of the first allele by encoding each nucleotide symbol of at least the portion of the first allele using two bits of binary data; and
 generate the encoded information corresponding to at least the portion of the second allele by encoding each nucleotide symbol of at least the portion of the second allele using two bits of binary data.

18. The non-transitory machine-readable medium of claim 16, wherein the record further includes a start position of the particular location in the sequence for the corresponding portion of the genome data.

19. The non-transitory machine-readable medium of claim 16, wherein the instructions, when executed by the one or more processors, further cause the one or more processors to:
 generate a plurality of additional records, each additional record corresponding to an additional respective portion of the genome data having an additional respective particular location in the sequence, each additional record comprising:
  a respective first length corresponding to at least a respective portion of a respective first allele associated with the additional respective particular location,
  a respective second length corresponding to at least a respective portion of a respective second allele associated with the additional respective particular location,
  respective first encoded information corresponding to at least the respective portion of the respective first allele, and
  respective second encoded information corresponding to at least the respective portion of the respective second allele; and
 store the plurality of additional records in the compressed searchable random-access version of the sequence of genome data.

20. The non-transitory machine-readable medium of claim 19, wherein each of the plurality of additional records further includes a respective start position of the additional respective particular location in the sequence for the additional respective portion of the genome data, and wherein the instructions, when executed by the one or more processors, further cause the one or more processors to:
 prior to storing the plurality of additional records, bundling at least one group of the plurality of additional records to form a bundle, by:
  setting a bundle start position for the bundle to the start position of a first record of the at least one group; and
  replacing the start position of each record of the at least one group with an offset from the bundle start position.

* * * * *